(12) United States Patent
Vadnais et al.

(10) Patent No.: US 7,349,130 B2
(45) Date of Patent: Mar. 25, 2008

(54) AUTOMATED SCANNING SYSTEM AND METHOD

(75) Inventors: Timothy W. Vadnais, Victoria, MN (US); Michael C. Marshall, Savage, MN (US)

(73) Assignee: GeoDigm Corporation, Chanhassen, MN (US)

( * ) Notice: Subject to any disclaimer, the term of this patent is extended or adjusted under 35 U.S.C. 154(b) by 912 days.

(21) Appl. No.: 10/133,538

(22) Filed: Apr. 25, 2002

(65) Prior Publication Data

US 2003/0002089 A1 Jan. 2, 2003

Related U.S. Application Data

(60) Provisional application No. 60/288,905, filed on May 4, 2001.

(51) Int. Cl.
*H04N 1/04* (2006.01)
*A61K 6/10* (2006.01)
*A61C 13/00* (2006.01)

(52) U.S. Cl. .................. 358/474; 264/16; 523/109

(58) Field of Classification Search .......... 235/454, 235/462.01, 462.46; 433/53, 24, 213; 358/496, 358/474, 1.6, 505, 449, 481, 497, 484, 493, 358/494, 498, 506, 509, 510, 513, 527; 264/16; 523/109; 271/3.03, 3.04, 3.05, 3.08, 145; 75/955; 249/64
See application file for complete search history.

(56) References Cited

U.S. PATENT DOCUMENTS 3,984,684 A * 10/1976 Winnek .................. 378/41
4,675,498 A * 6/1987 Lemelson .............. 219/121.62
4,773,029 A * 9/1988 Claesson et al. ............. 702/167
RE34,511 E * 1/1994 O'Neill et al. .............. 600/425
5,900,636 A * 5/1999 Nellemann et al. ..... 250/363.04
5,912,695 A * 6/1999 Kenbeek ...................... 347/262
6,233,474 B1 * 5/2001 Lemelson .................... 600/411
6,400,980 B1 * 6/2002 Lemelson .................... 600/478
6,579,095 B2 * 6/2003 Marshall et al. ............. 433/213
6,584,894 B1 * 7/2003 Mason .......................... 101/35
6,594,006 B1 * 7/2003 Muehlhoff et al. ...... 356/139.03
2002/0091316 A1 * 7/2002 Foo et al. ..................... 600/420
2002/0179711 A1 * 12/2002 Hileman ...................... 235/454

FOREIGN PATENT DOCUMENTS

GB 2189594 A * 10/1987
JP 408289884 * 11/1996

* cited by examiner

*Primary Examiner*—Jerome Grant, II
(74) *Attorney, Agent, or Firm*—Merchant & Gould P.C.

(57) ABSTRACT

A system and method for mass, automated scanning of objects, including dental study casts, housing parts, and other objects. The system and method are able to function with little or no human operator intervention, thereby facilitating high volume scanning and reducing scanning costs. The system includes a scanner having a scanning table, a conveyor mechanism adjacent the scanner for delivering objects to be scanned to the scanner, and a pick and place mechanism for taking an object from the conveyor mechanism and mounting it onto the scanning table of the scanner.

14 Claims, 8 Drawing Sheets

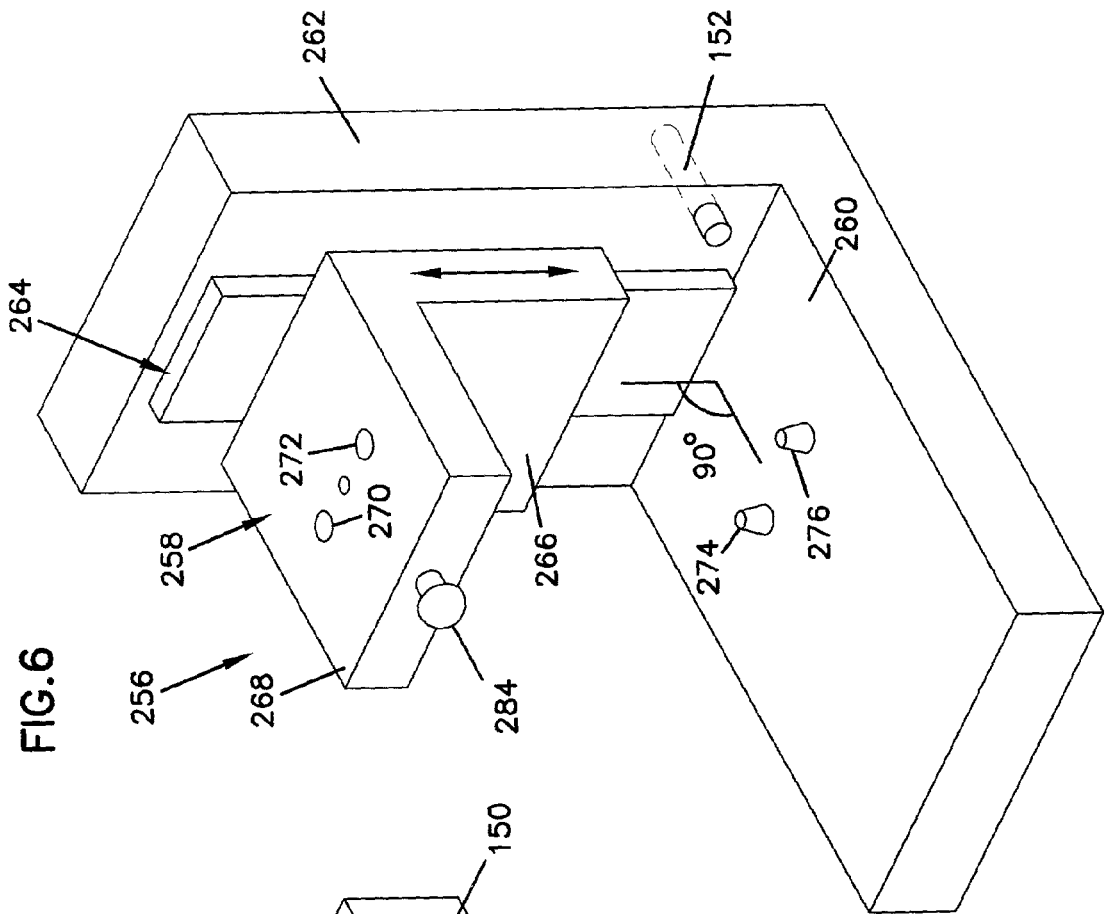
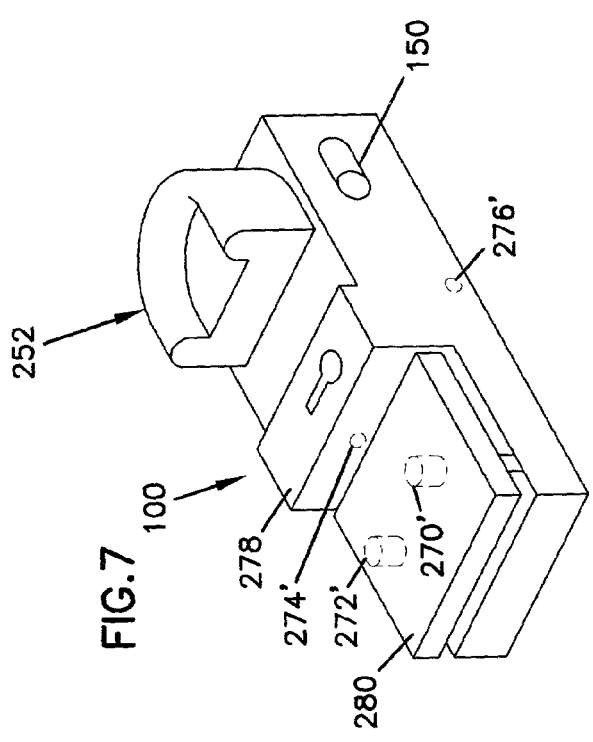

AUTOMATED SCANNING SYSTEM AND METHOD

This application claims priority from provisional application Ser. No. 60/288,905, filed May 4, 2001, and which is incorporated herein by reference.

FIELD OF THE INVENTION

The present invention relates generally to scanning of objects. More particularly, the invention relates to mass automated scanning of objects, such as dental study casts, housings for electronic devices including cellular telephones and electronic organizers, and other objects.

BACKGROUND OF THE INVENTION

Scanning of three-dimensional objects is generally known from the prior art. As disclosed in commonly assigned U.S. Pat. No. 6,217,334, dental study casts are scanned, and the data obtained from scanning the study casts is used for a variety of purposes, such as displaying a three-dimensional image of the static bite relationship of a particular patient for diagnostic and teaching purposes, or creating similar study casts in a suitable fabrication device based upon the scan data. Using the teachings from U.S. Pat. No. 6,217,34, individual objects can also be scanned for displaying a three-dimensional image of the objects or for use in fabricating similar objects based upon the scan data.

Scanning can also be used to verify a mating relationship between mating housing parts, such as housing parts for electronic devices including cellular telephones and electronic organizers. When housing parts are scanned, the scan data can be used to display three-dimensional images of the parts, with the displayed images being electronically brought together and displayed as a three-dimensional image, from which the accuracy of the fit between the housing parts can be determined.

Although scanning of objects is previously known, extensive human operator interaction is typically required in conventional scanning processes to monitor the process. For example, an operator typically must be present to load as well as unload the object(s) to be scanned onto and from the scanner. The need for human interaction in the scanning process creates problems. If the object is not loaded properly onto the scanner by the operator, inaccurate scan data can result. Further, the presence of an operator adds a labor cost to the scanning process, thereby increasing overall costs. Costs are increased even further if scanning is to be performed 24 hours a day, which is necessary for scanning large numbers of objects. In this case, additional employees must be hired for second and third shifts in order to operate and monitor the scanner.

Therefore, there is a need for an automated scanning system and method which reduces or eliminates the need for operator interaction, thereby facilitating mass scanning operations, improving the accuracy of the scan data and reducing the costs associated with the scanning operation.

SUMMARY OF THE INVENTION

The present invention provides a system and method for mass, automated scanning of objects, including dental study casts, housing parts, and other objects. The system and method are able to function with little or no human operator intervention, thereby facilitating high volume, automated scanning and reducing scanning costs.

In one aspect of the invention, a scanning system is provided. The system comprises a scanner having a scanning table, a conveyor mechanism adjacent the scanner for delivering an object to be scanned to the scanner, and a pick and place mechanism for taking the object from the conveyor mechanism and mounting it on the scanning table of the scanner.

In yet another aspect of the invention, a method of scanning of objects by a scanner having a scanning table is provided. The method comprises conveying one or more objects to be scanned to the scanner using a conveyor mechanism; picking an object from the conveyor mechanism and mounting the object on the scanning table of the scanner; scanning the object; and removing the scanned object from the scanning table and delivering the scanned object to a discharge location.

In still another aspect of the invention, a system for mass, automated scanning of dental study casts is provided. The system comprises a scanner having a scanning table, and a plurality of cassettes, each of which has a maxilla and mandible study cast for a single patient mounted thereon in known positions relative to each another. The system also includes a conveyor adjacent the scanner for delivering the cassettes to the scanner; and a pick and place mechanism engageable with the cassettes for picking one of the cassettes from the conveyor and mounting the picked cassette on the scanning table.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying description, in which there is described a preferred embodiment of the invention.

BRIEF DESCRIPTION OF THE DRAWINGS

Referring to the drawings, wherein like numerals represent like parts throughout the several views:

FIG. 6 illustrates an exemplary tool used to implement the automated scanning system and method according to a preferred embodiment of the present invention.

FIG. 7 illustrates a cassette used with the tool of FIG. 6.

DETAILED DESCRIPTION OF THE PREFERRED EMBODIMENT

A detailed discussion of a preferred embodiment of the automated scanning system and method of the present invention will be deferred pending a discussion of the concepts of the invention.

1. Overview

Figure 1:
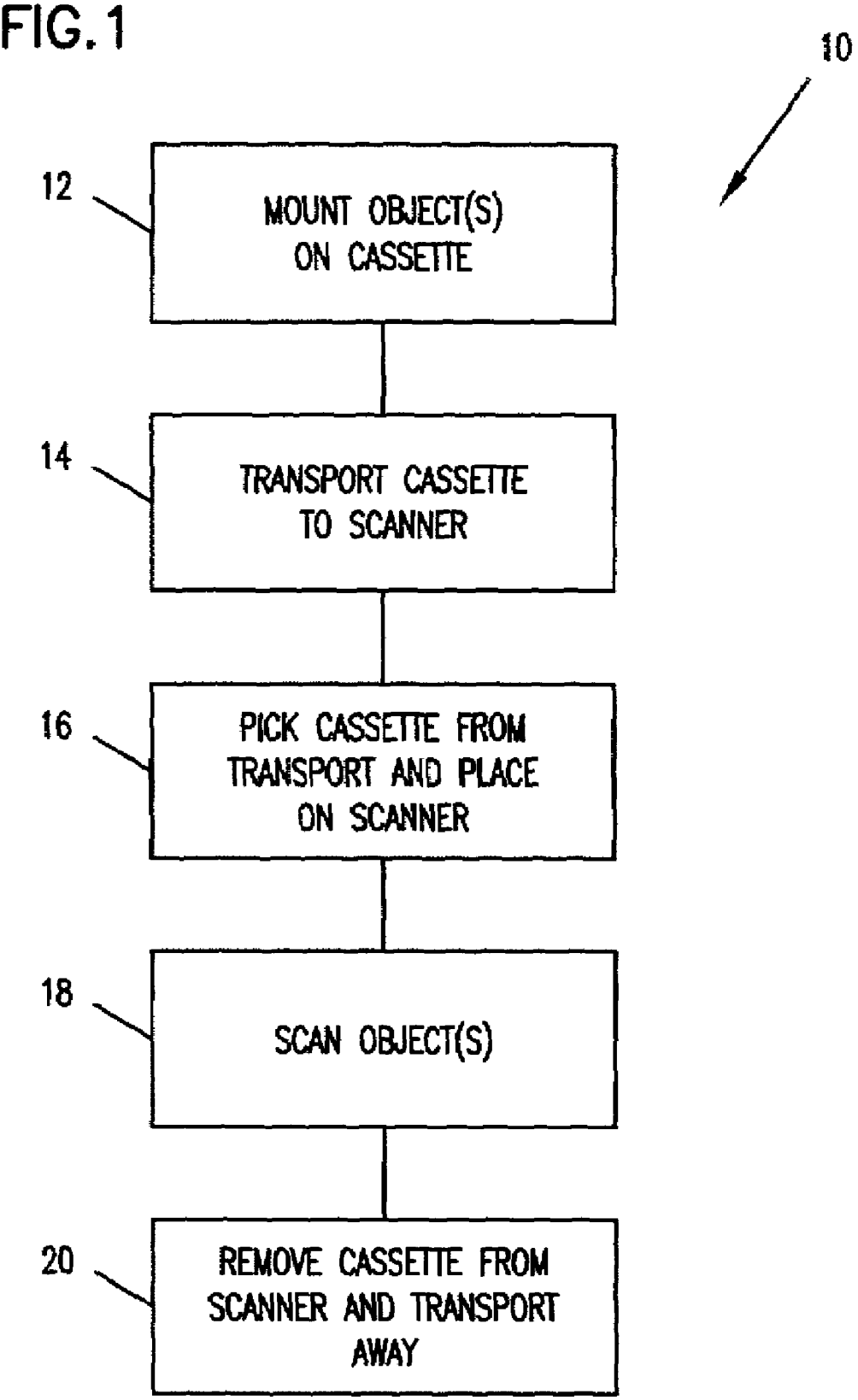
FIG. 1 illustrates the method steps used to practice the principles of the present invention.

Referring first to FIG. 1, the overall method of the present invention is illustrated, and is designated generally by the numeral 10. First, at block 12, the object(s) to be scanned is fixedly mounted onto a cassette. Any object(s) which one finds desirable to scan can be mounted onto the cassette. Examples of suitable objects include dental study casts and mating housing parts for electronic devices such as cell phones and electronic organizers. The preferred embodiment will be described below with respect to scanning dental study casts. The cassette and the procedure for mounting dental study casts on the cassette are described below with respect to FIGS. 6-9.

At block 14, the cassette is transported to the scanner by a suitable transport mechanism, and at block 16, the cassette is picked from the transport by a picking mechanism and placed onto a table 32 of a scanner 30. The transport mechanism and picking mechanism are described below and best seen in FIGS. 3-5.

Once the cassette is properly mounted, the object(s) is then scanned at block 18. In the preferred embodiment described below, two dental study casts are mounted on the cassette and the data obtained from scanning the study casts is used to create and display study cast images. The scan data can also be used to fabricate replicas of the study casts in a fabrication device based upon the scan data. In the preferred embodiment, the scanner 30 is a laser scanner with a laser 31 that is capable of movements along x-y-z axes to permit scanning of the complex geometries of dental study casts. However, other scanning concepts can also be used to practice the system and methods described herein, such as digitizing scanning.

Next, at block 20, once the scan of the object(s) is complete, the cassette is removed from the scanner by the picking mechanism and placed onto a transport for subsequent transport away from the scanner. As described in the preferred embodiment below, the transport that conveys a scanned object(s) away from the scanner is preferably a transport mechanism that is separate from the transport mechanism that conveys the object(s) to the scanner. However, a single transport mechanism could be used to both convey the object(s) to and away from the scanner. It is also contemplated that instead of conveying the cassette away from the scanner after scanning, the cassette could be placed in a suitable discharge location for later removal.

Figure 2:
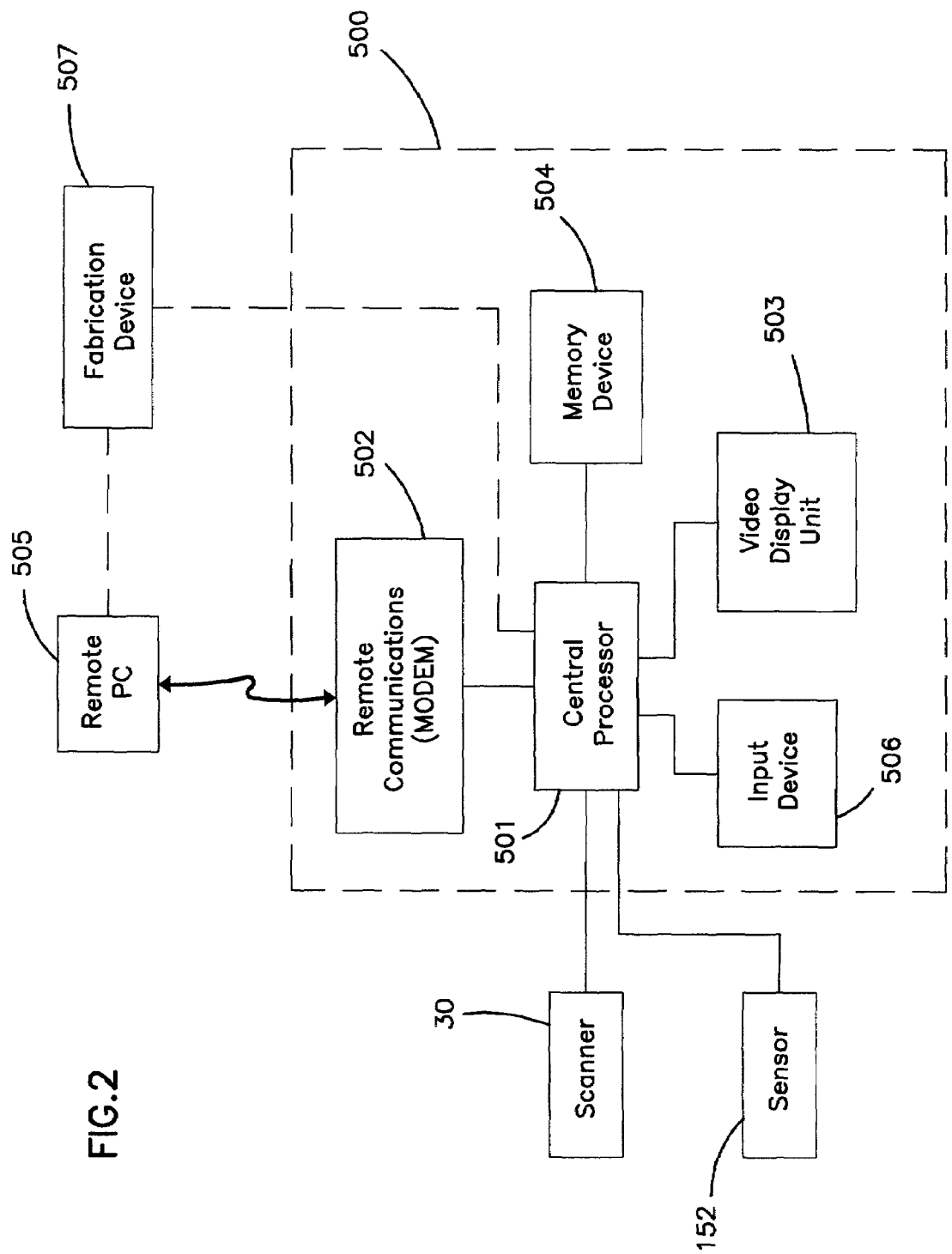
FIG. 2 diagrammatically illustrates functional blocks associated with the scanning process and processing data from the scanner.

With reference to FIG. 2, the image data obtained from the scanner 30 is processed by processor 501 of a computer 500 to create the image(s) of the scanned object(s), which in the preferred embodiment is the dental study casts. The processing by the processor 501 may include converting the scan data into images for display on a video display unit 503; converting the scan data into CNC or other format of output for use by a fabrication device 507 (also known as a prototyping apparatus); storing the scan data in a memory location or device 504; and/or transmitting the scan data to a remote processor 505 via modem block 502. A user input device 506 permits input commands to control operation of the scanner, as well as permits the input of information concerning the object(s) to be scanned.

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and readonly memory devices. Further, the modem 502 is illustrated to show a communications capability. Such capability may also be by way of a network, etc.

Fabrication device 507 may be connected directly to the computer 500 or may be connected to the remote computer 505. The fabrication device 507 may be any number of devices which can utilize computer generated data and create a threedimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM1500.

Further details on scanning, in the preferred embodiment, dental study casts and processing the image data can be found in U.S. Pat. Nos. 6,217,334, 6,206,693, and 6,200,135, which are incorporated herein by reference.

2. Automated Scanning

The preferred embodiment will now be discussed. In the preferred embodiment, a pair of dental study casts 250, 252 are mounted onto a cassette 100 for scanning by the scanner 30. The study casts 250, 252 are three-dimensional models of a patient's maxilla (i.e. upper) and mandible (i.e. lower) sets of teeth, respectively. The specifics of creating dental study casts from impressions that are taken of a patient's teeth is well known in the art. See, for example, U.S. Pat. Nos. 6,217,334, 6,206,693, and 6,200,135.

Figure 3:
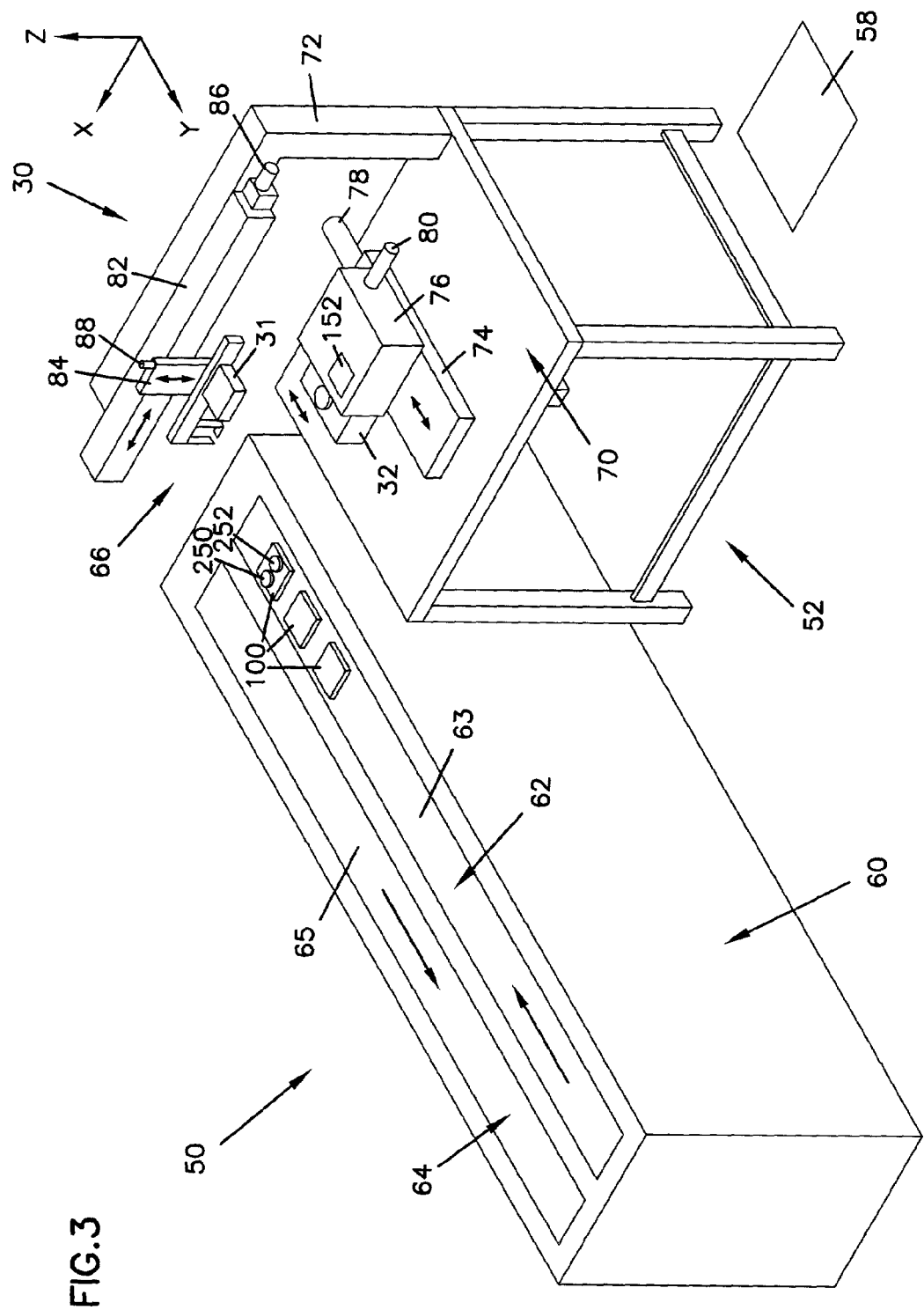
FIG. 3 is a perspective view of an automated scanning system according to the present invention.
Figure 4:
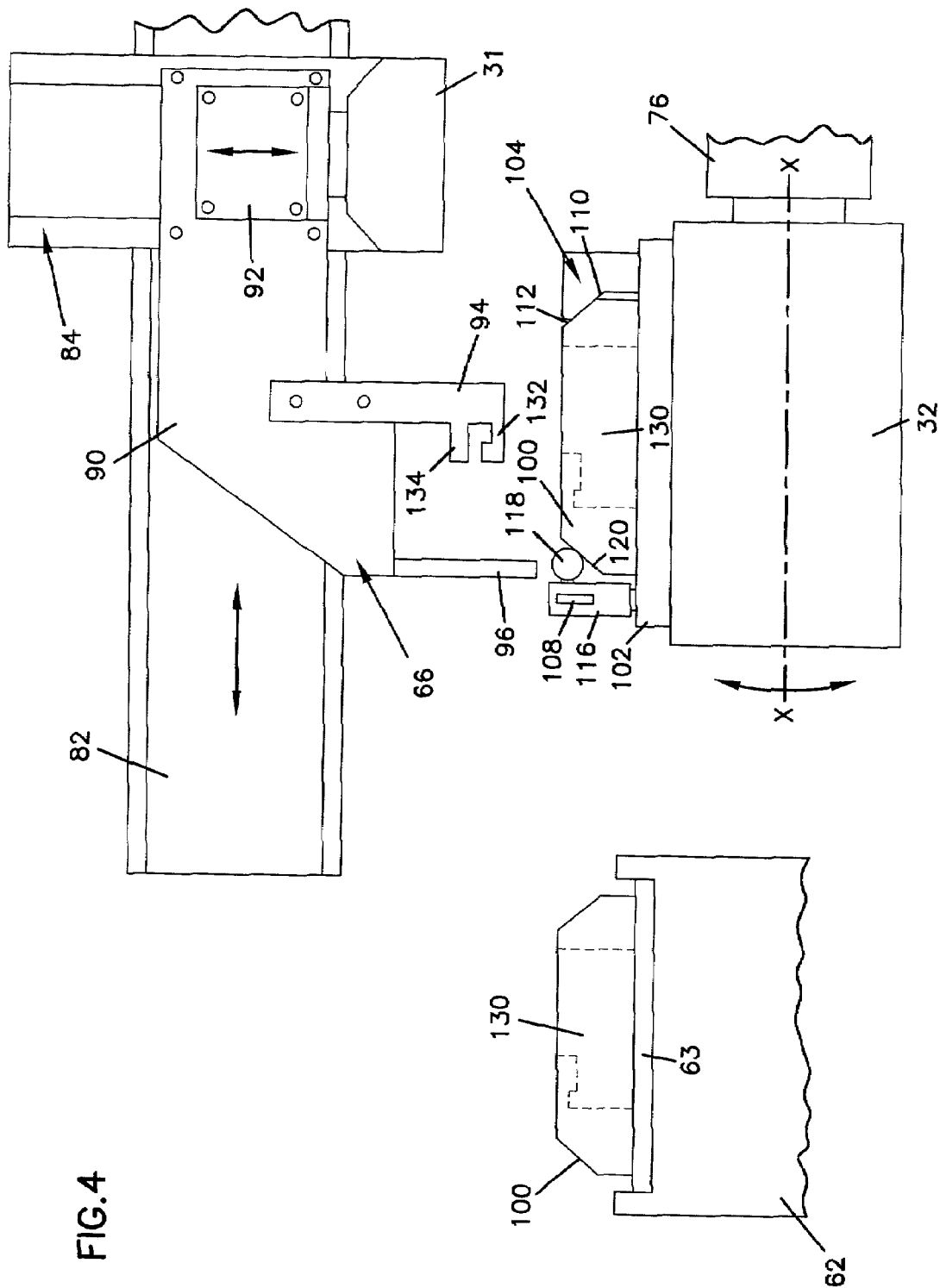
FIG. 4 illustrates a portion of the scanner and the infeed conveyor.
Figure 5:
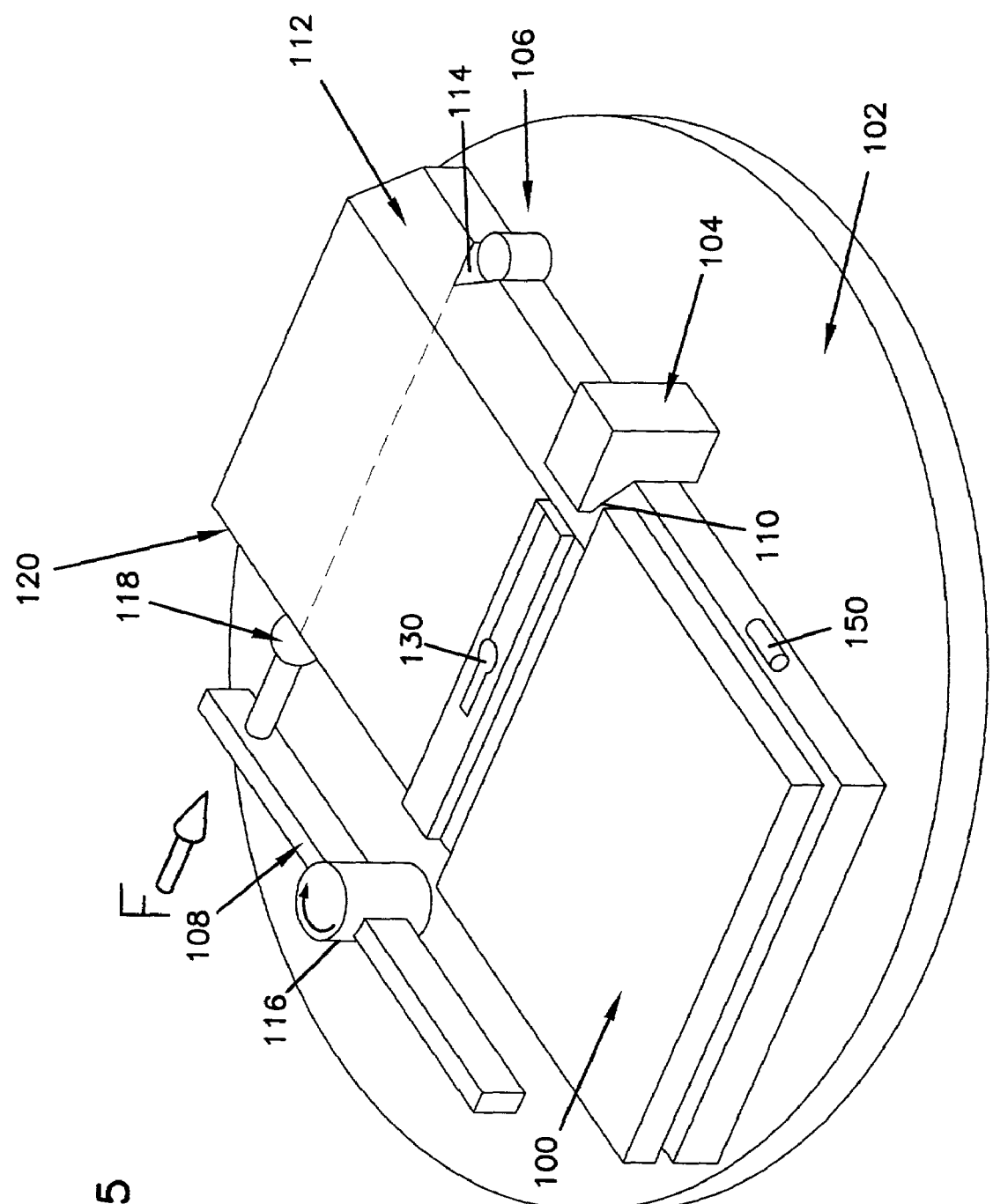
FIG. 5 is a perspective view of the rotary table of the scanner.

Turning now to FIGS. 3-5, a system 50 to achieve automated scanning of the study casts is illustrated. Prior to explaining the system in detail, some of the difficulties that are faced in implementing automated scanning will be discussed. An automated scanning system should be able to operate with minimal or no operator input. This reduces the costs associated with scanning, and increases throughput of the system because the system is able to run essentially all the time, day and night, with minimal operator input.

One of the primary factors in being able to implement automated scanning of dental study casts is the ability to achieve an accurate bite registration of the images that result from the scanned upper and lower study casts. Without some basis by which the computer is able to properly register the scanned images of the upper and lower casts, an accurate visual representation of the bite registration cannot be achieved. Therefore, a suitable method for achieving bite registration is needed. A bite registration method that is suitable for use with the automated scanning system 50 is described later in this specification, as well as in copending U.S. patent application Ser. No. 09/746,468, filed on Dec. 22, 2000.

Returning now to FIGS. 3-5, the automated scanning system 50 includes a scanning station 52 at which the study casts 250, 252 are scanned by the scanner 30. The scanner 30 is preferably a laser scanner as discussed above. Alternatively, other scanning concepts can be used, such as a digitizing scanning. Regardless of the particular scanner that is utilized, the scanner 30 is capable of scanning both the upper and lower casts 250, 252, with the scan data therefrom being processed by the computer 500 as discussed above. An operator input station 58 is provided that preferably includes a controller, such as the computer 500, for controlling operation of the system 50. The station 58 also preferably includes the display unit 503 and input device 506 for displaying system information and allowing operator inputs, such as system operation commands and patient data for each pair of study casts to be scanned.

The system 50 further includes a conveyor mechanism 60 for transporting the cassettes 100 to and from the station 52. The conveyor mechanism 60 includes an infeed conveyor 62 with a conveyor belt 63 upon which the cassettes 100 with the study casts 250, 252 mounted thereon are placed for subsequent feeding to the station 52. The conveyor mechanism 60 further includes an outfeed conveyor 64 with a conveyor belt 65 that feeds the cassettes 100, after scanning, to a downstream location for subsequent handling. Alternatively, the outfeed conveyor 64 could be eliminated, and the conveyor 62 extended past the station 52 so that the conveyor 62 acts both as the infeed conveyor and the outfeed conveyor. In addition, conveying mechanisms other than belts can be used.

Each cassette 100 is picked by a pick and place mechanism 66, best seen in FIGS. 3 and 4, from the infeed conveyor 62 and placed onto the table 32 of the scanner 30 where it is fixed in place for scanning. After scanning, the cassette 100 is removed from the table 32 by the pick and place mechanism 66 and placed onto the outfeed conveyor 64 for subsequent handling.

The system 50 permits automated, mass scanning of dental study casts, as well as other objects. As long as the system 50 is able to correlate the scanned data from each pair of study casts with a particular patient, such as through operator input via the input station 58 or by system identification of patient identifying indicia on the cassettes 100 or study casts 250, 252, the system is able to operate independently while performing its scanning and data collection functions, with little or no human operator interaction.

With reference to FIGS. 3 and 4, it is seen that the scanner 30 is mounted on a support structure 70, such as a table, located adjacent the conveyor mechanism 60. An L-shaped support arm 72 of the scanner 30 extends upwardly from the support 70 and towards the conveyor mechanism 60. A y-axis slide 74 is fixed on top of the support 70, and a support 76 for the rotary table 32 is mounted on the y-axis slide 74 so as to movable along the y-axis. An actuator 78, such as a reversible electric motor, is mounted to the slide 74 and is in driving engagement with the support 76 for actuating the support 74 along the y-axis. An actuator 80, such as a reversible electric motor, is also mounted to the support 76 and is in driving engagement with the rotary table 32 for rotating the table 32 about a central axis X-X.

An x-axis slide 82 is fixed to the overhanging portion of the support arm 72 to allow movement of the laser 31 along the x-axis. In addition, a z-axis slide 84 is mounted to the x-axis slide 82 to allow movement of the laser 31 along the z-axis. An actuator 86, such as a reversible electric motor, is mounted to the x-axis slide 82 and is in driving engagement with the z-axis slide 84 for actuating the z-axis slide 84 along the x-axis. In addition, an actuator 88, such as a reversible electric motor, is mounted to the z-axis slide 84 and is in driving engagement with a support arm 90 for actuating the support arm 90 along the z-axis. The support arm 90 forms part of the pick and place mechanism 66 and supports the laser 31.

Therefore, the laser 31 of the scanner 30 is mounted for linear movements along the x-axis slide 82 and the z-axis slide 84. Further, the scanning table 32 is mounted for linear movement along the y-axis slide 74, as well as for rotary movement about the axis X-X. The entire surface area of the study casts 250, 252 can thus be completely scanned through suitable movements of the laser 31 or the study casts 250, 252 along the x-y-z axes and about the X-X axis.

FIG. 4 illustrates the details of the pick and place mechanism 66 that is used to pick a cassette 100 from the conveyor 62 and place the cassette 100 on the rotary table 32 for scanning of the study casts 250, 252. The mechanism 66 is also used to remove the cassette from the rotary table and place it onto the conveyor 64. The laser 31 is fixed to the support arm 90 of the pick and place mechanism 66 through a laser support 92, whereby the laser 31 moves up and down along the z-axis when the arm 90 is actuated along the z-axis slide 84. In addition, a cassette engagement finger 94 and a release finger 96 are fixed to the arm 90 at locations spaced from each other as shown in FIG. 4.

The mechanism for fixedly mounting the cassette 100 onto the rotary table 32 will now be described with reference to FIG. 5. The rotary table 32 includes a face plate 102 on the top surface thereof. A stop 104, a pin 106 and a spring loaded lever arm 108 are all disposed on top of the face plate 102 for interacting with the cassette 100 and retaining the cassette 100 on the rotary table 32.

The stop 104 includes a beveled surface 110 (also seen in FIG. 4) that is designed to engage a beveled edge 112 of the cassette 100. The pin 106 is positioned to interact with a notch 114 that is formed in the side of the cassette 100 and counteract a rotational force that is applied to the cassette 100 by the lever arm 108. The lever arm 108 includes a pivot post 116 that is pivotally mounted on the face plate 102 directly opposite the stop 104. The post 116 is resiliently biased by a spring or other suitable resilient means in order to provide a force F in the direction of the arrow against the cassette 100 thereby forcing the cassette 100 against the stop 104 and the pin 106. A tooling ball 118 is fixed to the lever arm 108 directly opposite the pin 106, and engages a beveled edge 120 on the cassette 100.

When the cassette 100 is disposed on the face plate 102, the force provided by the lever arm 108 pushes the cassette 100 against the stop 104 and the pin 106. Further, the engagement between the beveled surface 110 of the stop and the beveled edge 112, as well as between the tooling ball 118 and the beveled edge 120, create a downward force that presses the cassette downward against the face plate, firmly holding the cassette in place for subsequent scanning. The pin 106, because it is located directly opposite the tooling ball 118, counteracts any tendency for the cassette 100 to rotate about the stop 104 as a result of the force F applied by the lever arm 108.

The procedure for picking a cassette from the conveyor 62 and placing it onto the rotary table 32 using the pick and place mechanism 66 will now be described with reference to FIGS. 4 and 5. The cassette 100 is formed with a key hole slot 130 (shown in dashed lines in FIG. 4) proximate the center thereof and extending generally parallel to the x-axis slide 82. The cassette engagement finger 94 of the pick and place mechanism 66 includes a male tab 132 that has a shape that is complimentary to the slot 130. The finger 94 further includes tab 134 that engages the exterior of the cassette when the male tab 132 is within the slot 130. It is further evident from FIG. 4 that the removal finger 96, which is intended to engage the lever arm 108 and remove the bias force F, projects a distance below the male tab 132 for a purpose which will become evident.

In order to pick a cassette 100 from the conveyor 62, the z-axis slide 84 is actuated along the x-axis (i.e. to the left in FIG. 4) so that the finger 94 is positioned over the slot 130. The arm 90 is then actuated along the z-axis (i.e. downward in FIG. 4) so that the male tab 132 enters the slot 130. The z-axis slide 84 is then once again moved to the left to lock the male tab 132 in the slot 130, with the tab 134 engaging the exterior surface of the cassette 100 for stabilization purposes. The arm 90 is then lifted upward, thereby lifting the cassette 100 off of the conveyor 62. The z-axis slide 84 is then actuated to the right to bring the cassette to a position above the rotary table 32. The arm 90 is then lowered until the removal finger 96 is next to the inside surface of the lever arm 108, between the post 116 and the tooling ball 118. Then, by moving the z-axis slide 84 to the left, the finger 96 forces the lever arm 108 in the opposite direction about the post 116. The cassette 100 can then be lowered onto the face plate 102 by lowering the arm 90 further. Once the cassette 100 is fully lowered, the z-axis slide 84 is moved slightly to the right and the arm 90 is then raised, thereby removing the male tab 132 from the slot 130. As this occurs, the finger 96 disengages from the lever arm 108, and the biasing force F of the lever arm forces the cassette against the stop 104 and the pin 106, thereby firmly retaining the cassette on the rotary table for subsequent scanning.

Removal of the cassette 100 from the rotary table 32 after scanning occurs in a similar fashion to the mounting of the cassette. The finger 96 removes the force of the lever arm 108 as the male tab 132 is being locked into the slot 130. When the lever arm 108 has been moved sufficiently and the male tab 132 is firmly secured in the slot 130, the cassette 100 can be moved slightly to the left and lifted upward, thereby removing the cassette. The cassette 100 is then carried to the conveyor 64, or other suitable discharge location, for conveyance away from the scanner 30.

It is to be realized that the x-axis slide 82 and the arm 90 must be of sufficient dimensions so as to be able to reach the two conveyors 62, 64. When side-by-side conveyors 62, 64 are used, as illustrated in FIG. 3, the x-axis dimensions of the x-axis slide 82 and the arm 90 are generally increased. For the case of a conveyor 62 that is used as both the infeed and the outfeed, the x-axis dimensions of the x-axis slide 82 and the arm 90 need not be as large.

As was described above, a suitable method for achieving an accurate bite registration of the images that result from the scanned study casts 250, 252 is needed. FIGS. 6-9 illustrate one embodiment of how an accurate bite registration can be achieved. This method can be used with study casts 250, 252 that have roughly formed (i.e. not machined to precise geometric specifications) bases. In this method, the study casts 250, 252 are initially mounted on the cassette 100 in known locations relative to each other, prior to placement of the cassette 100 onto the conveyor 62 for conveyance to the scanner 30. Because the positioning of each study cast relative to the other is known, once scanning is complete, the scanned images can be brought into registration using predetermined reference points.

FIG. 6-9 illustrate the tooling and other apparatus used to implement this method. FIG. 6 illustrates a tool 256 that is provided with a precision vertical slide 258 that is mounted so as to move vertically up and down relative to the tool 256. The tool 256 includes a base 260 and a vertical support 262 provided with a guide rail 264. The slide 258 includes a base 266 that is slidable on the rail 264 and an arm 268 that overhangs the base 260. The arm 268 includes a pair of locating holes 270, 272 on the bottom surface of the arm 268 facing the base 260. In addition, the base 260 includes a pair of locating pins 274, 276.

FIG. 7 illustrates the cassette 100 upon which the study casts 250, 252 are to be mounted. The study cast 252 is schematically illustrated in position on the cassette 100. The cassette 100 includes a ridge 278 that separates the cassette into two halves, the first half receiving the study cast 252 and the second half receiving the study cast 250. A removable plate 280, upon which the study cast 250 is to be mounted, is provided on the second half of the cassette 100. A pair of locating holes 274', 276' are formed in the bottom of the cassette 100 which interact with the locating pins 274, 276, respectively, so as to permit mounting of the cassette onto the base 260 of the tool 256. In addition, the removable plate 280 includes a pair of locating pins 270', 272' formed on the bottom thereof that are designed to fit within the locating holes 270, 272, respectively, on the arm 268 of the slide 258. The second half of the cassette 100 includes holes (not visible) that receive the locating pins 270', 272' when the plate 280 is disposed on the cassette.

Figure 9:
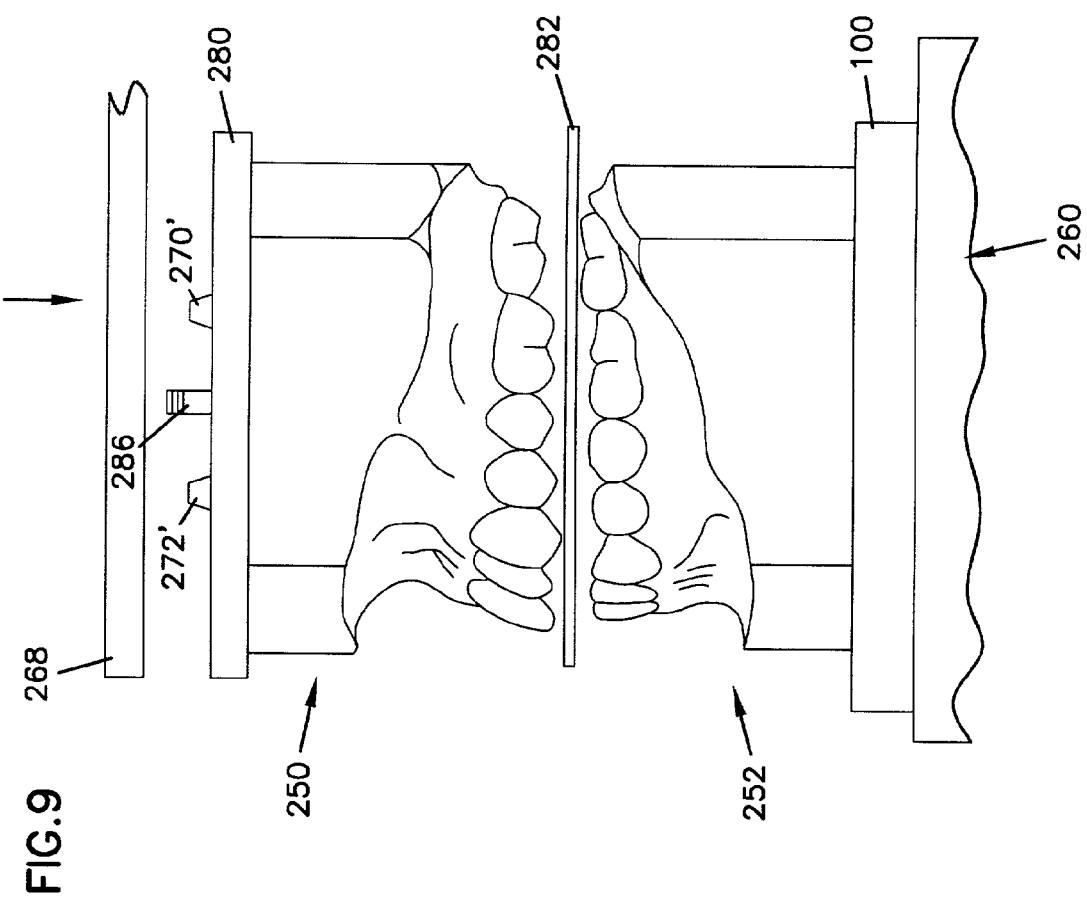
FIG. 9 schematically illustrates the use of the tool and cassette in FIGS. 6 and 7.

With reference to FIG. 9, in implementing this method, the study cast 252 is first fixed onto the first half of the cassette 100 such as by using hot melt glue or other suitable temporary fastening means. The cassette 100 is then mounted onto the base 260 of the tool 256 via the locating pins 274, 276 and locating holes 274', 276', with the study cast 252 disposed underneath the arm 268 of the slide 258.

A wax wafer 282, or other similar impression material, which has been previously bit into by the patient corresponding to the study casts 250, 252 to record the patient's bite registration, is then placed onto the study cast 252. The wafer 282 is placed onto the study cast so that the impression that corresponds to study cast 252 fits onto the teeth of the cast 252. The study cast 250 is then placed on top of the wafer 282 with the teeth fitting into their corresponding impressions in the wafer. It should be realized that the wafer 282 permits the study casts 250, 252 to be registered with each other while on the tool 256. Once the study casts are registered, the plate 280 is fixed onto the bottom surface of the study cast 250 such as by using hot melt glue or other fixing means.

The slide 258 is then slid downward, either manually using a knob 284 fixed to the arm 268 or through suitable mechanical means (not illustrated), toward the plate 280. The arm 268 then captures the plate 280, with the locating pins 270', 272' fitting into the locating holes 270, 272. A fastener 286 connected to the plate 280 extends upwardly through a hole provided in the arm 268 to permit the plate 280, and the study cast 250 now fixed thereto, to be fixed to the arm 268 so when the slide 256 is again raised, the study cast 250 and plate 280 are raised with the slide 256. Raising the slide 256 separates the study casts 250, 252 while precisely maintaining the relative positioning of the study casts so that the registration is maintained.

After the slide 258 is raised, the plate 280, with the study cast 250 fixed thereto, is removed from the arm 268, flipped over so that the study cast 250 faces upward, and mounted onto the second half of the cassette 100 so that both study casts are now fixed on the cassette. The cassette can then be placed onto the conveyor 62 for transport to the scanner so that the study casts can be scanned to create scanned images. It should be realized that the study casts are mounted on the cassette 100 in positions that maintain the bite registration of the patient. However, what is also needed are reference points so that the images resulting from the scan can be aligned.

Figure 8:
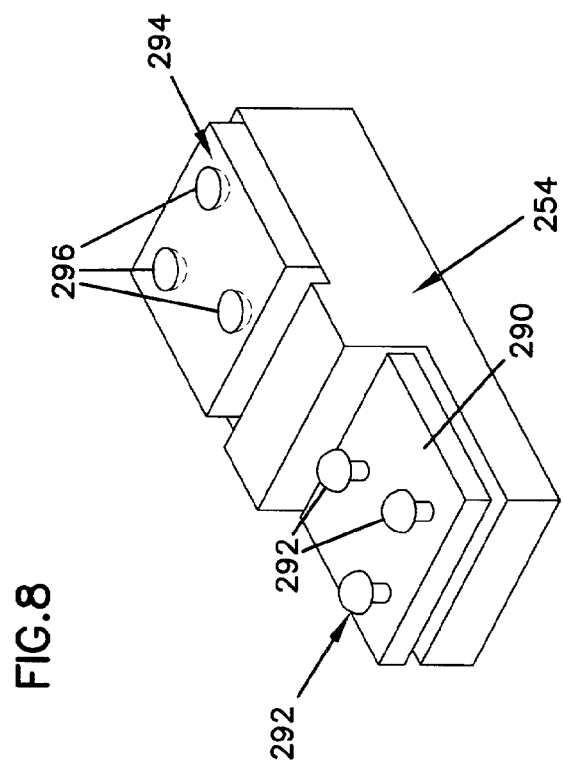
FIG. 8 illustrates a calibration procedure for determining reference points.

Reference points are used in this method to achieve alignment, with the reference points being determined in accordance with a calibration process illustrated in FIG. 8. The calibration process is performed prior to mounting the study casts on the cassette. To perform calibration, the cassette 100 is provided with a removable plate 290, in place of the plate 280. The plate 290 includes a plurality of tooling balls 292 thereon. In the preferred embodiment, three tooling balls 292 are used, however a larger number of tooling balls could also be used. A layer of clay 294 or other impression material is placed on the other half of the cassette 100. The cassette 100 is then mounted on the tool 256 as discussed above, with the clay 294 located underneath the arm 268, and the plate 290 is mounted on the arm 268 with the tooling balls 292 facing downward toward the clay 294. The slide 258 is then moved downward until the balls 292 move into the clay 294 in order to form tooling ball impressions 296. The slide 258 is then moved upwardly and the plate 290 removed therefrom and remounted onto the cassette 100.

The cassette 100 is then mounted onto the rotary table 32 of the scanner 30, as discussed above, and the scanner scans the tooling balls 292 and the impressions 296. Mounting of the cassette can be done using the pick and place mechanism 66, or manually. By scanning the tooling balls 292 and impressions 296, the computer 500 can find the centers of the balls 292 and impressions 296, with the centers providing fixed reference points for use in aligning subsequently scanned study casts. These fixed reference points are retained within the memory device 504, so that the computer 500 knows ahead of time the reference points to be used. Due to the construction of the tool 256 and the cassette 100, the relative positions of the centers of the tooling balls 282 and the centers of the impressions 296 correspond to identical positions on the study casts 250, 252. Therefore, once the images of the study casts are generated, the three fixed points can be aligned to register the scanned impressions. After the points are aligned, the scanned images can be brought together by the computer 500 to a position representative of the patient's actual bite registration. The reference points are fixed in system memory, so that once the study casts are properly positioned on the cassette 100, the scanning and registration can be completed automatically by the computer 500, without requiring further operator input. It is further contemplated that the use of the tool 256 and the related process of positioning the study casts on the cassette 100 can be automated as well.

Periodically, the calibration process should be repeated so as to obtain updated reference points. This is necessary due to loosening of tolerances and general degradation of equipment.

As part of the automation of scanning, the system 50 needs to know which of the study casts 250, 252 being scanned belong to which patient, so that the scan data can be saved to the appropriate memory location belonging to that patient in the memory device 504. To accomplish this objective, the cassette 100 can be provided with a patient identification tag 150, such as a radio frequency tag, a bar code or other suitable means. The tag 150 can contain patient data such as the patient's name and address, as well as more extensive patient data pertaining to the patient's past medical history, such as previous dental procedures. A sensor 152 is provided at a suitable location, such as on the support 76 as shown in FIG. 3, to read the tag 150. The sensor 152, as is shown in FIG. 2, is connected to the central processor 501 of the computer so that the information that is read from the tag 150 is provided to the computer. The sensor 152 can be located at any convenient point in the system 50, such as on the tool 256 as shown in FIG. 6. However, it is preferred that the sensor 152 be positioned at a location so that it performs a read of the tag 150 just prior to, or immediately after, scanning of the study casts 250, 252.

The preferred embodiment of the invention has been described in relation to automated scanning of dental study casts. However, as discussed above, the concepts described herein can also be used in implementing automated scanning of a variety of other objects as well. For instance, automated scanning can be applied to parts that are to be mated together, such as molded housing shells for cellular phones, electronic organizers, pacemakers, and a host of other parts having complex geometries. When applied to mated parts, the accuracy of the parts, and the molds used to create the parts, can be verified by scanning the parts and determining from the scanned images whether a suitable fit between the parts will be achieved. This verification can be performed at the manufacturing level by the supplier of the molded parts as the molded parts are molded, or at an assembly level by the user of the molded parts to ensure the quality of received parts. Molded parts can include plastic molded parts, metal parts formed by metal molding techniques, and mating parts formed from other materials and other molding techniques suitable for those other materials.

Figure 10:
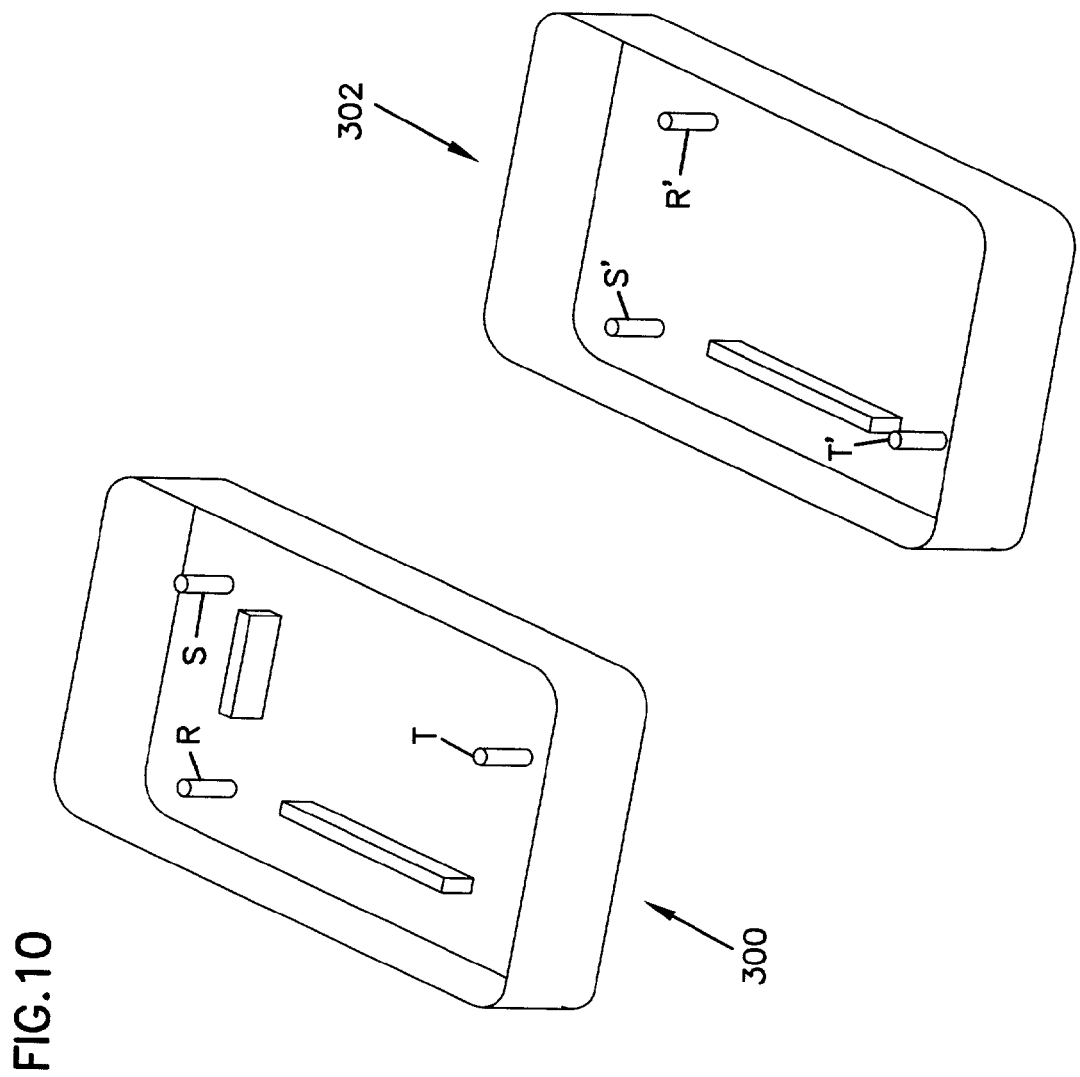
FIG. 10 schematically illustrates a pair of housing shells that can be scanned in order to verify their mating relationship.

FIG. 10 illustrates a pair of housing shells 300, 302 that are to be mated together to form a housing for a device such as a cellular phone, electronic organizer or a pacemaker. The inside of each housing shell 300, 302 is schematically illustrated to show an example of the possible complex geometry inside each shell. In use, the shell 300 is flipped over and mated with the shell 302 to enclose the electronics and other components of the device formed by the mated shells 300, 302. The shells 300, 302 can be scanned and images created from the scan data in order to display the mating relationship (i.e. "verify" the parts) to determine whether the shells fit together adequately. A plurality of reference points would have to be used to achieve alignment of the shell images once they are scanned. For instance, three points R, S, T on the shell 300, and three points R', S', T' on the shell 302, corresponding to, for example, mounting posts on the shells 300, 302, could be used to align the images once the shells are scanned. The method described above for registering the dental study casts could also be used to register the shells 300, 302.

In addition, automated scanning can be applied to single objects that are not mated or fitted with a corresponding object. For instance, single objects can be scanned for subsequent display of an image of the object created from the scan data, or the scan data can be used to fabricate a replica of the object based upon the scan data.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A scanning system for scanning a plurality of dental study casts, comprising:
   a laser scanner, said scanner arranged and configured to collect data relating to the shape of the dental study casts;
   a plurality of cassettes upon which the dental study casts to be scanned are mounted, wherein the dental study casts include both maxilla and mandible study casts mounted on each of said cassettes;
   a conveyor mechanism adjacent said scanner for delivering said cassettes to said scanner, whereby the dental study casts are delivered to said scanner; and
   a pick and place mechanism for taking said cassettes from said conveyor mechanism and mounting it on said scanner.

2. The system of claim 1, wherein said laser scanner is mounted for movement along at least two mutually perpendicular axes.

3. The system of claim 2, wherein said scanner includes a scanning table that is mounted for movement along an axis perpendicular to said two mutually perpendicular axes, and wherein said scanning table is rotatable.

4. The system of claim 1, wherein said conveyor mechanism includes an infeed conveyor and an outfeed conveyor.

5. The system of claim 1, further including an operator input station adjacent said scanner.

6. The system of claim 1, further including an identification tag fixed to each of said cassettes.

7. The system of claim 6, wherein each of said identification tags includes information relating to the dental study casts.

8. A method of scanning of objects by a scanner having a scanning table, comprising:
   a) conveying objects to be scanned to the scanner using a conveyor mechanism, wherein the objects are dental study casts, and further including mounting maxilla and mandible study casts patient on one cassette;
   b) picking an object from the conveyor mechanism and mounting the object on the scanning table of the scanner;
   c) scanning the object without intermediate steps and collecting data on the physical shape of the object; and
   d) removing the scanned object from the scanning table and delivering the scanned object to a discharge location.

9. The method of claim 8, further including:
   picking an additional object to be scanned from the conveyor mechanism, and mounting the additional object on the scanning table, and repeating steps c) and d).

10. the method of claim 8, wherein mounting the object on the scanning table comprises mounting the cassette on the scanning table whereby the maxilla and mandible study casts are scanned together.

11. The method of claim 8, further including mounting the maxilla and mandible study casts on the cassette in known positions relative to one another.

12. The method claim 8, further including reading an identification tag fixed to said cassette.

13. A system for mass, automated scanning of dental study casts, comprising:
   a scanner having a scanning table;
   a plurality of cassettes, each said cassette having a maxilla and mandible study cast for a single patient mounted thereon in known positions relative to each another;
   a conveyor adjacent the scanner for delivering the cassettes to the scanner; and
   a pick and place mechanism engageable with said cassettes for picking one of said cassettes from said conveyor and mounting the picked cassette on said scanning table.

14. The system of claim 13, wherein said scanner is a laser scanner.

* * * * *